(12) United States Patent
Ivaldi et al.

(10) Patent No.: US 8,541,741 B2
(45) Date of Patent: Sep. 24, 2013

(54) PHOTONIC MEASUREMENT INSTRUMENT USING FIBER OPTICS

(75) Inventors: Juan C. Ivaldi, Redding, CT (US); Paul L. St. Cyr, Shelton, CT (US); Eugene Chow, Singapore (SG); Mark C. Werner, Brookfield Center, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 220 days.

(21) Appl. No.: 12/949,383

(22) Filed: Nov. 18, 2010

(65) Prior Publication Data

US 2011/0122396 A1 May 26, 2011

Related U.S. Application Data

(60) Provisional application No. 61/263,142, filed on Nov. 20, 2009.

(51) Int. Cl.
*G01J 5/00* (2006.01)

(52) U.S. Cl.
USPC .................................................. 250/338.1

(58) Field of Classification Search
USPC .................................................. 250/338.1
See application file for complete search history.

(56) References Cited

U.S. PATENT DOCUMENTS

| 4,432,644 | A  | * | 2/1984  | Demers et al. ................ 356/316 |
| 5,315,528 | A  | * | 5/1994  | L'vov ............................ 702/23 |
| 5,880,823 | A  |   | 3/1999  | Lu |
| 6,542,231 | B1 | * | 4/2003  | Garrett .......................... 356/246 |
| 7,671,985 | B1 | * | 3/2010  | Milosevic et al. ............ 356/326 |
| 2009/0316740 | A1 | * | 12/2009 | Zhu et al. ........................ 372/34 |

FOREIGN PATENT DOCUMENTS

| JP | 62-103539 | 5/1987 |
| JP | 62103539  | 5/1987 |

* cited by examiner

*Primary Examiner* — Christine Sung
(74) *Attorney, Agent, or Firm* — Cesari and McKenna, LLP

(57) ABSTRACT

A photonic measurement system, such as an atomic absorption spectrometer, includes source, sample and detection modules that are interconnected by fiber optic cables. A first set of fiber optic cables guides light from one or more light sources in the source module to each of at least two analysis chambers in the sample module. A second set of fiber optic cables guides light from the analysis chambers to a detector in the detection module. The detector provides to a processing sub-system signals that correspond to intensities of the guided light. One analysis chamber is selected to perform a sample analysis at a given time, and the processing sub-system processes the signals associated with the selected analysis chamber as measurement signals. The processing sub-system may further process the signals associated with a given non-selected analysis chamber as reference signals.

26 Claims, 8 Drawing Sheets

PHOTONIC MEASUREMENT INSTRUMENT USING FIBER OPTICS

CROSS REFERENCE

The present application claims the benefit of U.S. Provisional Patent Application Ser. No. 61/263,142, which was filed on Nov. 20, 2009, by Juan C. Ivaldi et al. for an ATOMIC ABSORPTION INSTRUMENT USING NON-SOLARIZING UV GRADE FIBER OPTICS and is hereby incorporated by reference.

BACKGROUND OF THE INVENTION

1. Field of the Invention

The invention relates generally to photonic measurement instruments and, more particularly, to high-precision atomic absorption instruments.

2. Background Information

Atomic absorption instruments, such as spectrometers, are well known and are used in a variety of settings. The atomic absorption instruments of interest are high-precision systems that include precisely aligned optics that tightly couple measurement light, that is, light of an appropriate wavelength for absorption analysis, to samples. The high-precision systems also utilize additional light sources and associated optics to provide reference paths to determine and compensate for light intensities as well as correct for background absorption. The systems of interest utilize simultaneously operating measurement and reference light paths, as described in U.S. Pat. No. 6,222,626, which is incorporated herein in its entirety by reference.

As described in the patent, a precisely aligned configuration of mirrors and beam splitters is used to direct the light from the measurement and background correction light sources, for example, a hollow cathode lamp "HCL" and a Deuterium (D2) lamp, simultaneously to the start of each of the measurement path and the reference path. The measurement path then uses a further plurality of precisely aligned mirrors to couple the light to a sample within an atomizer and also direct light from the atomizer to a detector, while the reference path uses optical fibers to guide the light to the detector.

The atomizer operating in the atomic absorption spectrometer is commonly either a flame (nebulizer) or a furnace, such as a graphite tube. Certain atomic absorption spectrometers can operate with more than one type of atomizer, and include manually or automatically operated mechanical mechanisms that move one atomizer, for example, a flame chamber, out of the optical measurement path and move another atomizer, for example, a furnace, into the optical measurement path. The movement of the atomizers often necessitates a re-alignment of the precisely aligned configuration of minors and beam splitters that direct light to the measurement path and/or the further plurality of minors that tightly couple the light to the sample. The re-alignment of the optics is both time consuming and complex, and results in system downtime.

Other known systems operate the atomizers in tandem, which works well if collimated light sources, such as lasers, are used. With light sources such as the HCLs and D2 lamps, however, the light beams diverge over the extended measurement path, and the optics of the tandem system are therefore quite complex and costly.

SUMMARY OF THE INVENTION

A photonic measurement instrument includes a first set of fiber optic cables that guide light directly and simultaneously from one or more light sources to each of a pair of analysis chambers, and a second set of fiber optic cables that directly and simultaneously guide light from the respective analysis chambers to a detector. A selector/mapper bundles the respective optical fibers that guide light directly from the light sources and, through mapping of the optical fibers, further guides the light from each of the light sources to both of the analysis chambers. A user selects which of the analysis chambers is to be used at a given time for sample measurement, and a system controller operates the selected analysis chamber as a component of the measurement path. At the same time, the other analysis chamber becomes a part of the reference path, to pass light between associated cables of the first and second sets of fiber optic cables. A processing sub-system then processes the signals associated with the selected analysis chamber as measurement signals and the signals associated with the non-selected analysis chamber as reference signals. Accordingly, the measurement and reference paths are simultaneously and interchangeably provided through the system by the selection of an analysis chamber, without requiring re-configuration of the system and/or re-aligning of system optics.

Alternatively, the reference path may be provided by a dedicated fiber optic cable, such that the selector/mapper maps the optical fibers along three paths through the system, namely, the dedicated reference path and the paths associated with the respective analysis chambers. The processing sub-system then processes the signals associated with the selected analysis chamber as the measurement signals and the signals associated with the dedicated reference path as the reference signals, and does not process the signals associated with the non-selected analysis chamber. In this configuration, the measurement path is simultaneously and interchangeably provided through the system by the selection of an analysis chamber, again without requiring re-configuration of the system and/or re-aligning of system optics.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
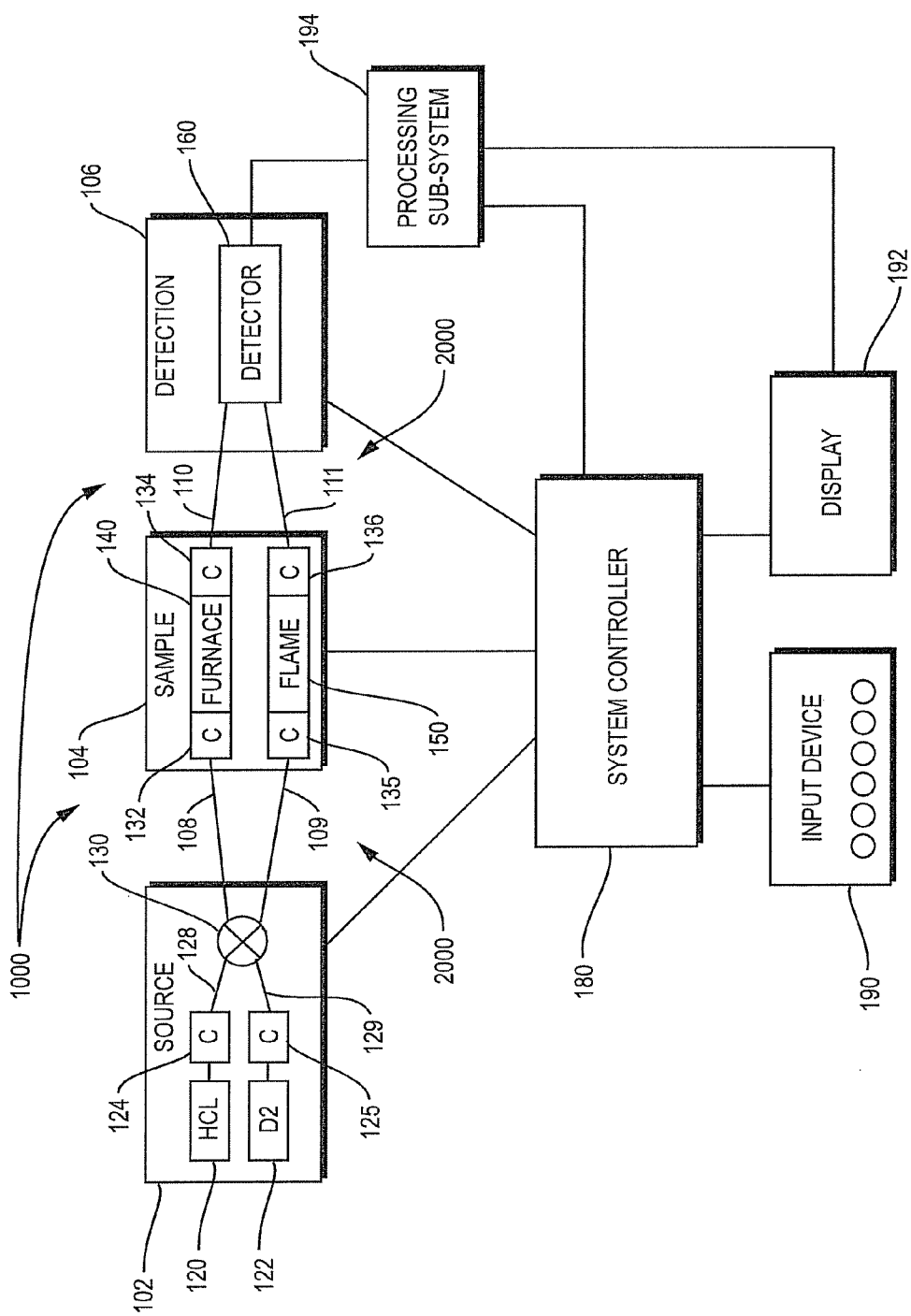
FIG. 1 is a functional block diagram of an atomic absorption spectrometer constructed in accordance with the invention.

The drawings are not to scale and certain components may be enlarged relative to other components for ease of explanation. The same reference numerals in different drawings refer to the same components. A photonic measurement instrument is described by example as an atomic absorption spectrometer. Other photonic measurement systems may be similarly configured, for example, systems employing inductively coupled plasma optical emission spectroscopy, optical detection in liquid chromatography, UV/visible spectroscopy and UV/visible near infrared spectroscopy. In such systems appropriate analysis chambers are utilized in the same manner as the atomizers discussed below.

Referring to FIG. 1, an atomic absorption spectrometer includes a source module 102, a sample module 104 and a detection module 106 that are interconnected by fiber optic cables 108-111 that are segments of paths 1000 and 2000 through the system. The source module includes two types of light sources 120 and 122, for example, a hollow cathode lamp (HCL) that operates at a desired wavelength for absorption analysis and a Deuterium (D2) lamp that provides light for background correction. The light produced by the light sources is guided directly from the light sources by fiber optic cables 128 and 129, which are also segments of the paths 1000 and 2000, respectively. The respective fiber optic cables 128 and 129 consist of multiple optical fibers.

A selector/mapper 130 included in the source module 102 bundles the optical fibers of the cables 128 and 129 and maps the fibers to fiber optic cables 108 and 109, which are branches that guide light from both sources simultaneously to each of two atomizers 140 and 150 in the sample module 104. The cables 128, 129, 108 and 109 form a first set of fiber optic cables. Fiber optic cables 110 and 111 guide light from the atomizers 140 and 150 in the sample module 104 to a detector 160 in the detection module 106. The cables 110 and 111, which form a second set of fiber optic cables, are also segments of the respective paths 1000 and 2000. In the example, the fiber optic cables in the first and second sets consist of non-solarizing UV grade optical fibers, which are appropriate for instruments that may operate with light wavelength ranges that are referred as "deep UV," such as, for example, down to 193 nm. For instruments operating in other wavelength ranges, the same or other optical fibers may be used.

The detector 160, which receives the light guided to it by the fiber optic cables 110 and 111, may be a monochromator that, as needed, utilizes slits or other mechanisms (not shown) to direct the light provided by the fiber optic cables to different regions of a single sensor. Alternatively, the detector may include two sensors (not shown) that are positioned appropriately to receive light directly from corresponding cables. The detector 160 operates in a known manner to produce signals that correspond to the intensities of the impinging light of selected wavelengths, and provides the signals to a processing sub-system 194.

A system controller 180 controls the operations of the components of the respective modules 102, 104 and 106 and the processing sub-system 194 based on a selection of an atomizer, as discussed in more detail below. The system controller is configured to receive signals from an input device 190, such as a computer keyboard or touch screen, through which a user provides atomizer selection instructions and, as appropriate, other instructions for the analysis. A display device 192 provides information to the user relating to system operation, as well as the results of the processing performed by the processing sub-system 194.

The atomizers 140 and 150 may be, for example, a flame chamber, or nebulizer, and a furnace, such as, for example, a graphite tube. A user enters instructions through the input device 190, to select which of the atomizers to use for sample measurement at a given time. In response to the instructions, the system controller 180 controls operation of the light sources 120 and 122 and the atomizers 140 and 150, to provide optical measurement, background correction and reference information to the detector 160.

More specifically, the system controller 180 operates the selected atomizer 140, 150 in a known manner to provide the light from which sample measurements and background correction information is obtained and operates the non-selected atomizer in a mode that allows light to simply pass through, to provide reference information. The system controller further controls the operation of the processing sub-system 194, such that the sub-system processes the signals associated with the selected atomizer as measurement path signals and the signals associated with the non-selected atomizer as reference path signals. The system controller thus instructs the processor sub-system to process signals provided from, as appropriate, a particular region of the sensor or a particular sensor as the measurement signals, and the signals from the other region or sensor as the reference signals.

The system thus allows a user to select either of the atomizers for sample measurement at any given time, without having to reconfigure the system. Notably, the selection of an atomizer does not require a mechanical movement of one or more atomizers into or out of the optical measurement path. Accordingly, in the system 100 the optics in the measurement path do not have to be re-aligned to change the atomizer included in the measurement path.

To optimize the system, fiber optic coupling units 124, 125 may be used within the source module 102 to couple the light produced by the light sources 120, 122 to the respective fiber optic cables 128 and 129. Within the sample module 104, fiber optic coupling units 132, 133 may be used to couple light from the cables 108 and 109 to designated areas, for example, the centers, of the respective atomizers 140, 150. Further, fiber optic coupling units 134, 136 may be used to couple light from the atomizers to the fiber optic cables 110 and 111, which then guide the light to the detection module 106. The coupling units are described in more detail with reference to FIGS. 2A-C.

Figure 2A:
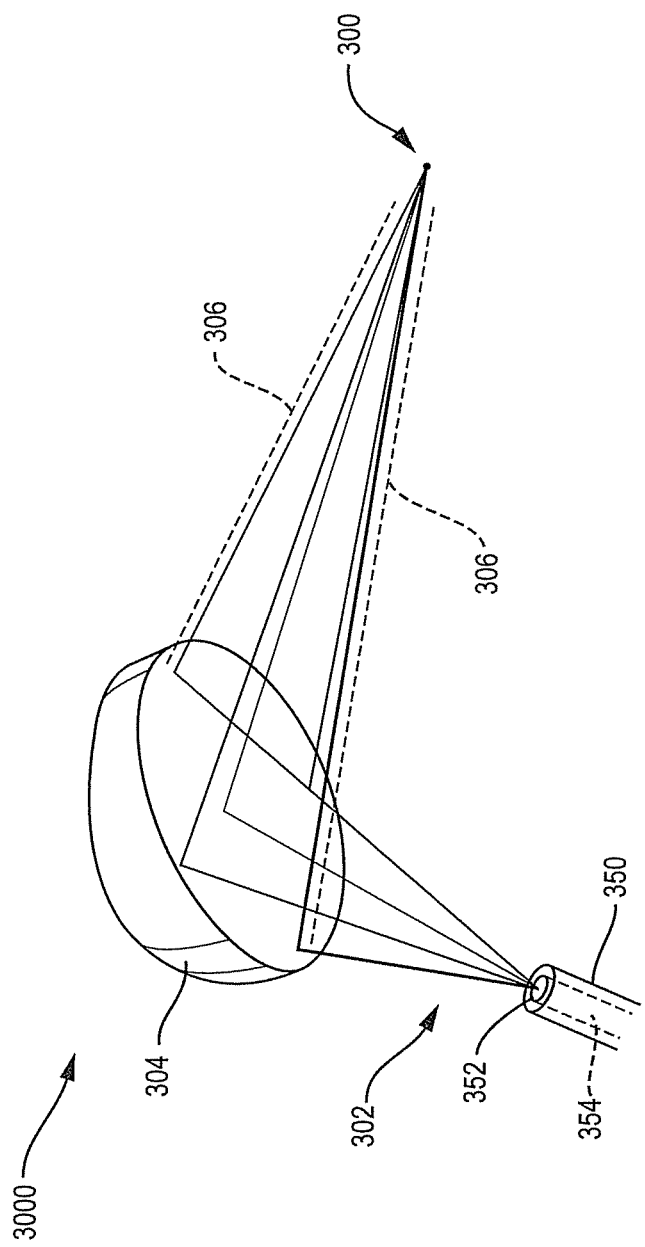
FIGS. 2A-2C are functional block diagrams of couplers depicted in FIG. 1.

Referring now to FIG. 2A, a representative coupling unit 3000 consists of a coupler 304, in the example, an off-axis elliptical mirror that couples light provided by a source 300 that is located at a first of two focal points of the mirror to a destination 302 that is located at the second focal point of the minor. In the example, the minor reflects the light with a 90° bend, though other degree bends, for example 30° or 60°, may be utilized by design.

The coupler 304 is essentially characterized by a ratio of the first and second focal lengths. For example, a 0.5× coupler has a destination that is twice as far from the mirror as the source. The coupler is further characterized by a clear aperture, which is a designated area of the mirror from which impinging beams are focused to the destination. The clear aperture, which is denoted by dotted lines 306 in the drawing, essentially determines the size of the mirror. The couplers may be utilized to change the numerical aperture of the beams, i.e., for reduction or magnification of the beams, all in a known manner.

The coupler 304 is preferably coated with a UV-enhanced coating. In the example, the coupler is coated with UV enhanced aluminum with greater than 85% reflectivity for the wavelengths of interest. In the system 100, the wavelengths of interest are 190 nm to 900 nm. As appropriate, a rectangular minor may be used instead of an elliptical mirror.

In the example depicted in FIG. 2A, the destination 302 is a core 354 of a fiber optic cable 350. The cable 350 is aligned with the coupler, or mirror, 304 such that the second focal point of the minor is within the entrance 352 of the core, which may consist of a single or multiple optical fibers.

In the system, each of the couplers couples light either to or from a fiber optic cable. The respective fiber optic cables are characterized by numerical apertures, as are the light sources 120, 122 and the entrances and exits 141, 151 and 143, 153 (FIG. 2C) of the atomizers 140, 150. The couplers preserve or change the numerical apertures of the beams and/or the magnification of the beams from one component to the next along the paths 1000 and 2000 as desired. In the example, the coupling units 124 and 125 are 0.5× couplers that reduce the numerical aperture of the beams, the coupling units 132 and 135 are 2× couplers that inflate the numerical apertures of the beams, and the coupling units 134 and 136 are 1× couplers that relay, or preserve the numerical apertures of, the beams.

Figure 2B:
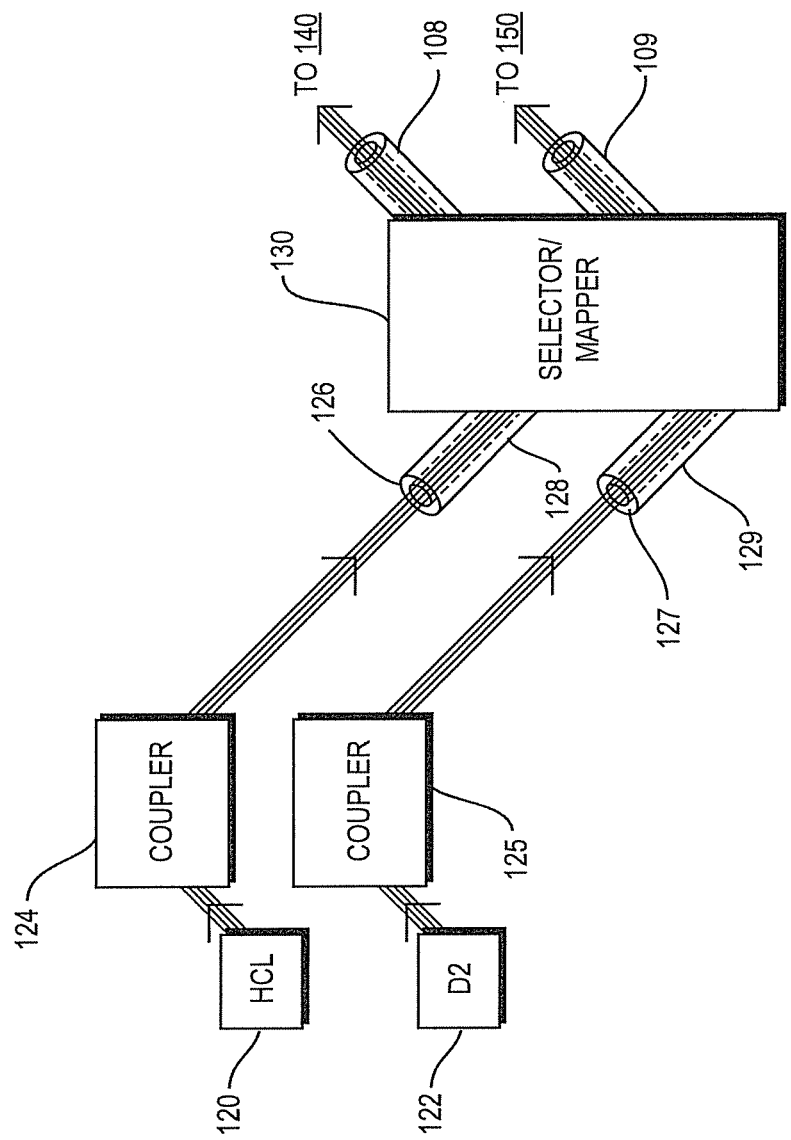

Referring now also to FIG. 2B, to configure the system, coupling units 124, 125 on the source module 102 are aligned with the light sources 120, 122 and the fiber optic cables 128, 129. The coupling units are thus positioned such that the light sources are at the first focal points of the corresponding couplers, or mirrors, and entrances 126 and 127 of fiber optic cables 128, 129 are at the second focal points of the mirrors. The fibers 129, 128 extend through the selector/mapper 130, which bundles and maps respective optical fibers to guide the light from each of the individual sources to both of the atomizers 140, 150 over cable sections 108, 109.

Figure 2C:
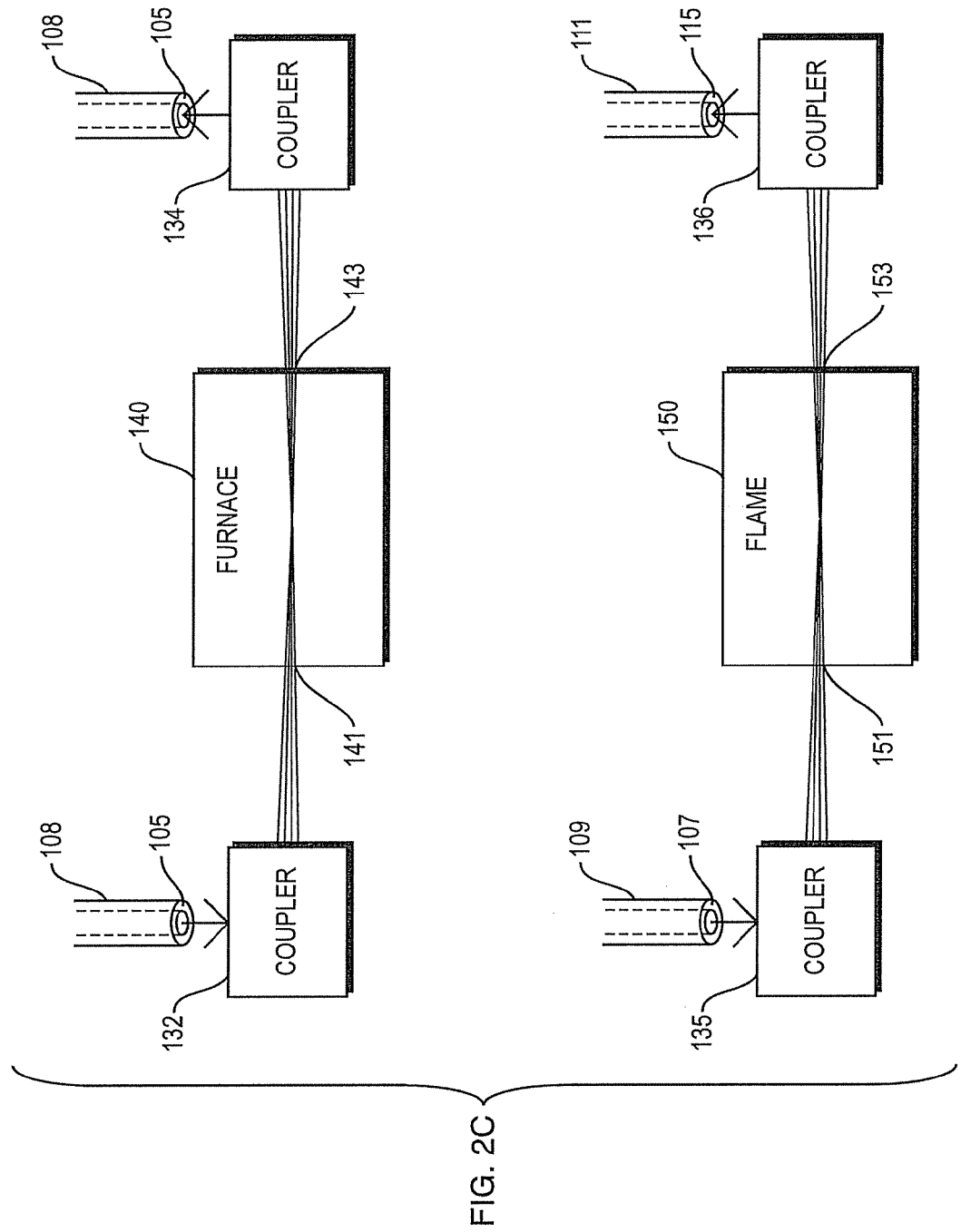

Referring now also to FIG. 2C, on the sample module 104, the ends 105, 107 of the cable sections 108, 109 are aligned with the coupling units, or couplers, 132 and 135 as sources and the couplers couple light from the fibers through respective entrances 141, 151 of the atomizers 140, 150 to the second focal points of the couplers which are, in the example, at the centers of the atomizers. Similarly, the coupling units 134 and 136 are aligned with exits 143, 153 of the atomizers, to couple light from the atomizer centers, as sources, to the entrances 113, 115 of fiber optic cables 110 and 111. Once the couplers and fibers are properly aligned on the source and sample modules 102, 104, the modules 102, 104, 106 may be moved relative to one another by the bending of any or all of the cables 108, 109, 110, 111. The relative movement of the modules does not adversely affect the alignment of the system optics, however, because the coupling units are located within the respective modules. For efficient system operation, the movement of the modules should not introduce a bend radius of less than 300 times the diameter of the smallest optical fiber of the bending fiber optic cable. The optical fibers may but need not be the same diameter over the entire system. Alternatively, the first and second sets of fiber cables may utilize optical fibers of different respective diameters. For ease of explanation, we have not shown in the drawings protective walls with quartz covered openings to allow light through, and so forth that are situated between the atomizers and the optics and serve to isolate the optics from corrosive vapors that may be present during analysis. The use of such walls is well known in atomic absorption instruments that utilize traditional optics and is employed in the current system for the same reasons.

The user-selectable and interchangeable paths for both measurement and reference signals provides a great deal of flexibility to not only the use of the system but also the configuration of the system. Specifically, the source, sample and detection modules 102, 104 and 106 can be arranged such that the heat sources for the respective atomizers 140, 150 are situated away from temperature sensitive system components. Further, in a system that is used to analyze volatile or radioactive materials, a given atomizer or both atomizers may be segregated from other system components.

Figure 3:
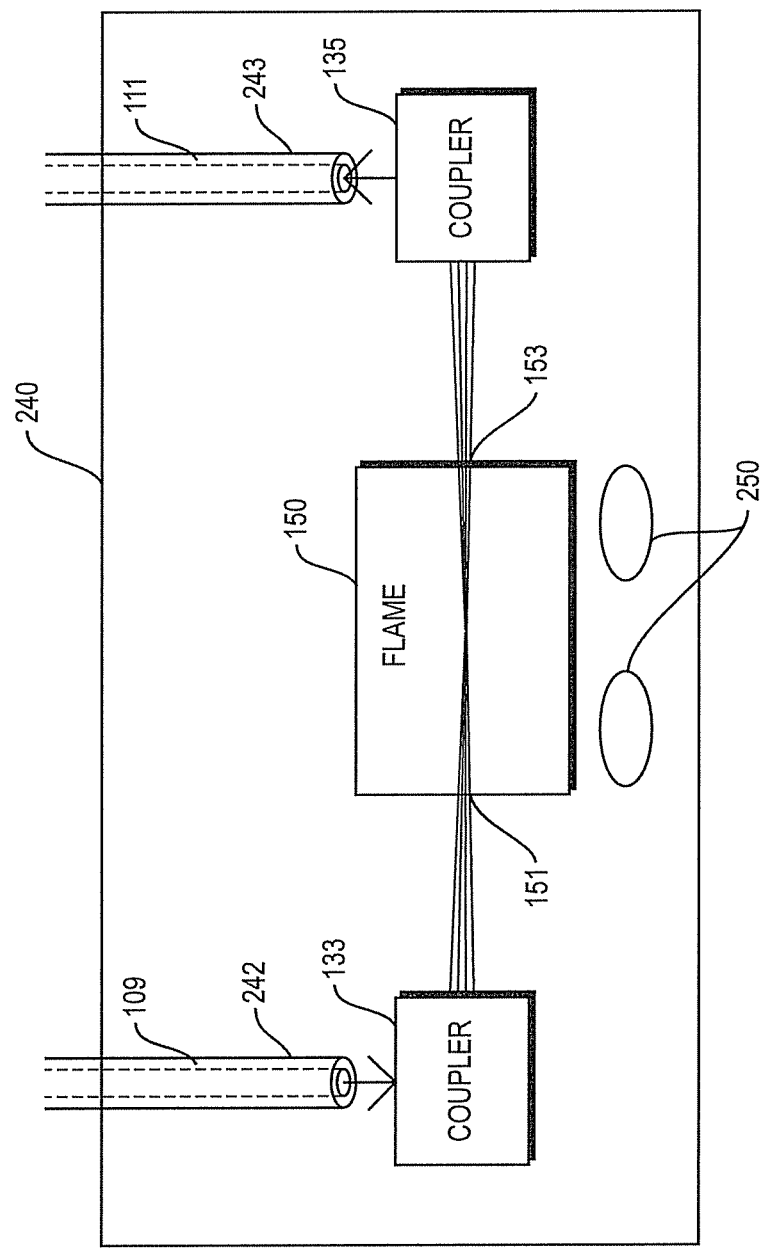
FIG. 3 depicts an alternative arrangement of an atomizer that is depicted in the system of FIG. 1.

For example, as shown in FIG. 3, an atomizer, which in the example is a flame chamber 150, is operated in a glove box 240, with optical feedthroughs 242 and 243 mounted to the walls of the glove box. The coupling unit 132, which is located inside the glove box, couples the light received through the optical feedthrough 242 through the chamber entrance 151 to the center of the flame chamber. The coupling unit 134, which receives light sourced the center of the flame chamber through the atomizer exit 153, couples the light through the optical feedthrough 243 into the core of the cable 110. A user has access to the atomizer through the gloved holes 250, in order to position the samples within the atomizer. The system controller operates the system as described above to perform the analysis, with the segregated atomizer 150 selected or not, as appropriate.

The respective modules 102, 104, 106 of the atomic absorption spectrometer 100 may be separately manufactured. Further, the respective modules may be optimized for particular uses, and thus, different system configurations may be assembled. For example, the modules manufactured for a given system may be optimized for use with light of particular wavelengths, and so forth. Also, as discussed, the sample module, for example, may be optimized for use with radioactive or other materials that require segregation of one or both of the atomizers.

Figure 4:
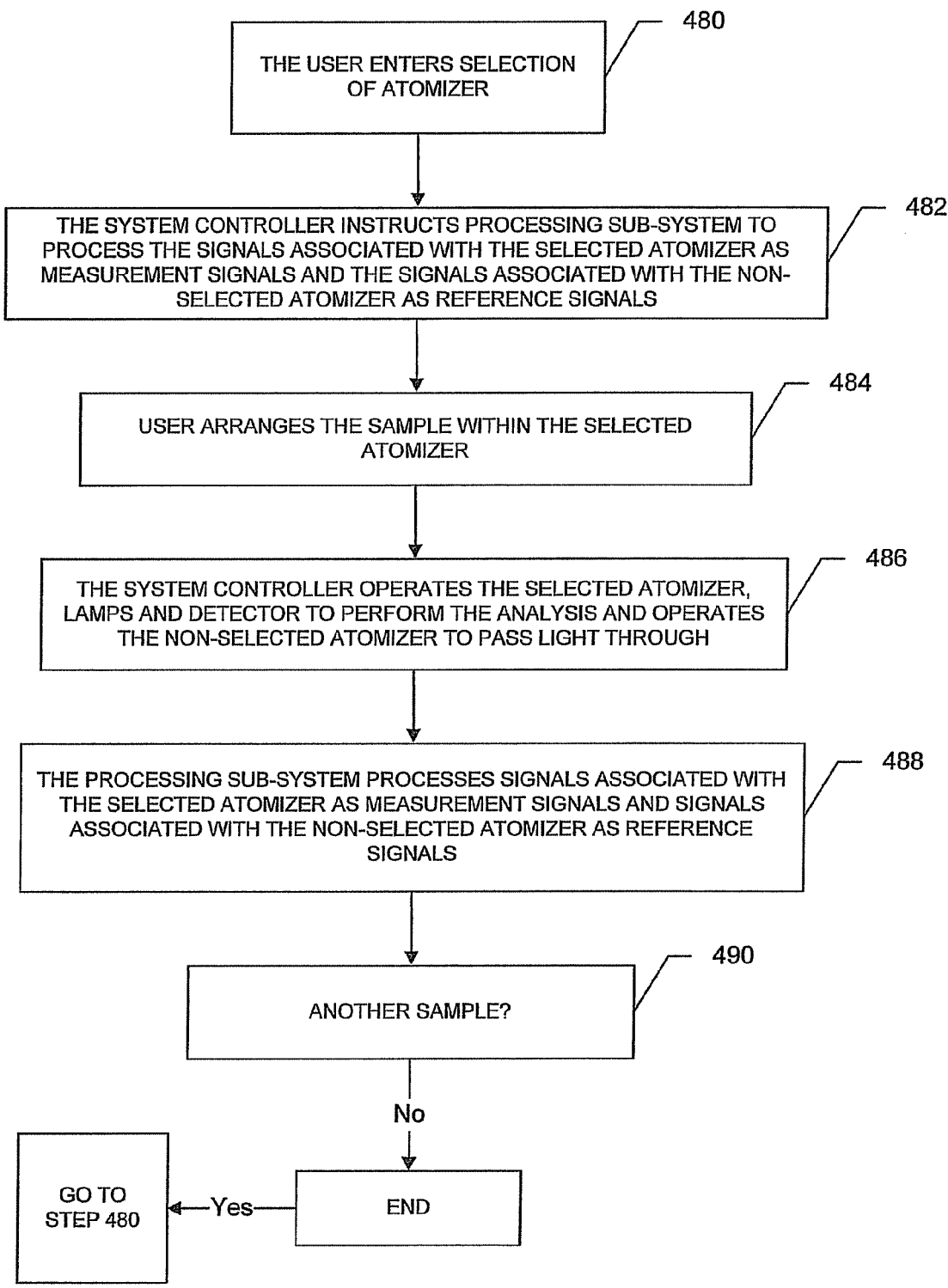
FIG. 4 is a flowchart of the operations of the system of FIG. 1.

Referring now also to FIG. 4, the operations of the atomic absorption spectrometer 100 are described. A user in step 480 enters into the system, through the input device 190, his or her selection of which of the atomizers 140, 150 to use for sample analysis. The user also, as appropriate, provides information and/or instructions relating to the analysis to be performed, such as, duration, temperature and so forth. Alternatively, the user may select a pre-programmed analysis routine.

In the example, the user selects the flame compartment 140. In response to the selection information, the system controller 180, in step 482, instructs the processing sub-system 194 to process signals associated with the selected atomizer as measurement signals and signals associated with the non-selected atomizer as reference signals. The system controller thus specifies that signals provided by a given sensor or given region of a sensor in the detector 160 are to be processed as measurement signals and signals from another sensor or region are to be processed as reference signals. In step 484, the user arranges the sample within the selected atomizer.

Once the sample is in place, the system controller, in step 486, operates the selected atomizer in a known manner to perform the requested analysis. In addition, the system controller operates the non-selected atomizer in a "stand-by" mode, in which the light provided by fiber optic cable to the atomizer is passed to the fiber optic cable leading from the atomizer to the detector. Further, the system controller operates the HCL and D2 lamp and the detector 160 in a known manner for the analysis.

The system controller 180 thus operates the light sources 120, 122 and the detector 160 in synchronism. In the example, the system controller operates the lamps and the detector in synchronous on and off cycles of, for example, 50 Hz. As is discussed in U.S. Pat. No. 6,222,626, which is incorporated herein by reference, the HCL and D2 lamp are operated separately for at least part of a detection cycle.

In step 488, the processor sub-system 194 processes the signals provided by the detector 160 in a known manner, in accordance with the instructions from the system controller as to which signals are measurement signals and which signals are reference signals.

The user may, in step 490, select the same or other atomizer for the analysis of a next sample, and the system controller operates the system accordingly.

Figure 5:
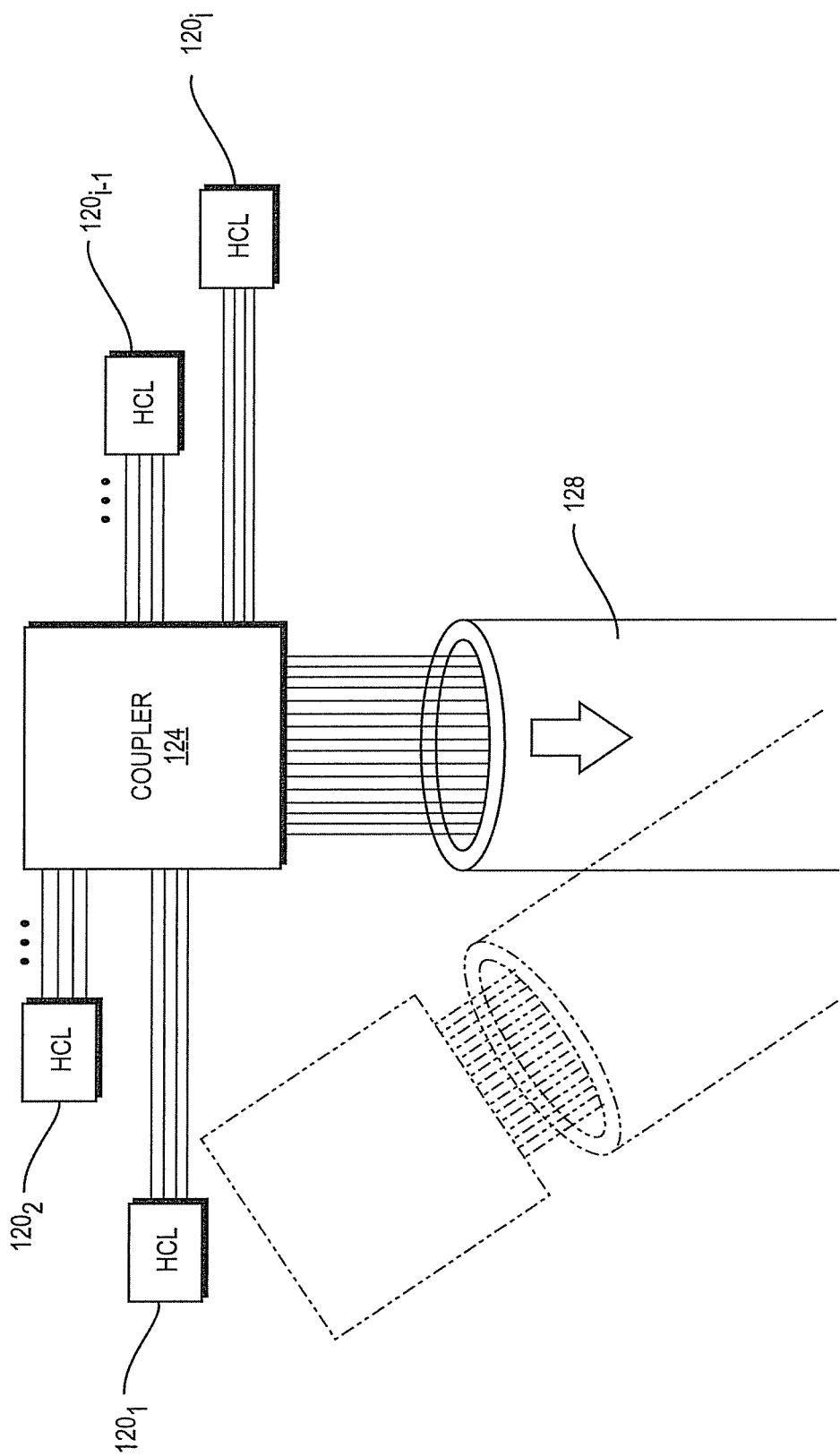
FIG. 5 is an alternative arrangement of a source module that is depicted in FIG. 1.

Referring now to FIG. 5, multiple HCLs $120_1, 120_2 \ldots 120_i$ of different wavelengths may be included in the source module 102. Alternatively, some or all of the light sources 120, may be electrodeless discharge lamps (EDLs). Multiple lamps may be positioned to operate simultaneously with the coupling unit with only a selected lamp or lamps operating at any given time or, as discussed below, the coupling unit may be re-positioned relative to a selected lamp. A user or the system controller selects which of the HCLs and/or EDLs to use for a given analysis, and the system controller then controls the operation of the selected lamp appropriately to perform the analysis.

The coupling unit 124 may be moveable relative to the HCLs and/or EDLs, by a slight bending of the fiber optic cable 128. The coupling unit is thus moved to a designated position (shown by dotted lines) proximate to the selected lamp, without altering the alignment between the coupler and the entrance 130 of the fiber optic cable 128. Alternatively, the lamps may be arranged on a turnstile (not shown) that rotates either under the control of the user or under system control to bring the selected lamp into position at the focal point of a stationary coupler, or both the lamps and the coupler may be moveable relative to one another to designated positions. In addition, multiple couplers and fiber optic cables may be used, with the respective optical fibers of the multiple cables being bundled through the selector/mapper 130 into the fiber optic cables 108, 109. With such an arrangement, the light of two or more wavelengths may also be provided to the atomizer simultaneously.

Figure 6:
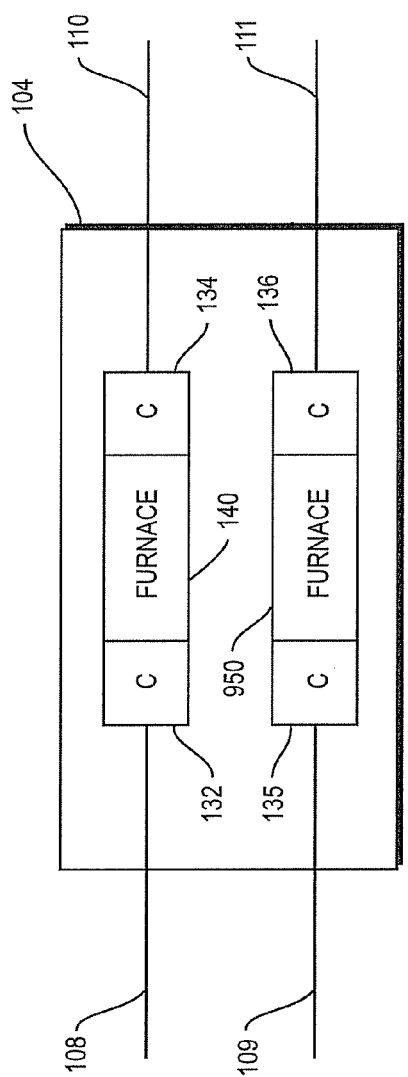
FIG. 6 is an alternate arrangement of a sample module that is depicted in FIG. 1.

Referring now also to FIG. 6, certain atomic absorption operations, for example, certain analyses that utilize the furnace 140, need not employ a reference signal. Accordingly, a sample module 104 may be constructed with two side-by-side in-line furnaces 140 and 950, such that the selected furnace operates while a user arranges a next sample to be analyzed in the non-selected atomizer. In response to system controller instructions, the processing sub-system 194 processes the signals from the selected atomizer as measurement signals. Presumably, the non-selected processor does not pass optical information through to the second set of fiber optic cables. The throughput of the system can thus be increased by the selectable and interchangeable use of the two furnace atomizers, without requiring a reconfiguration and/or re-alignment of the system components.

Figure 7:
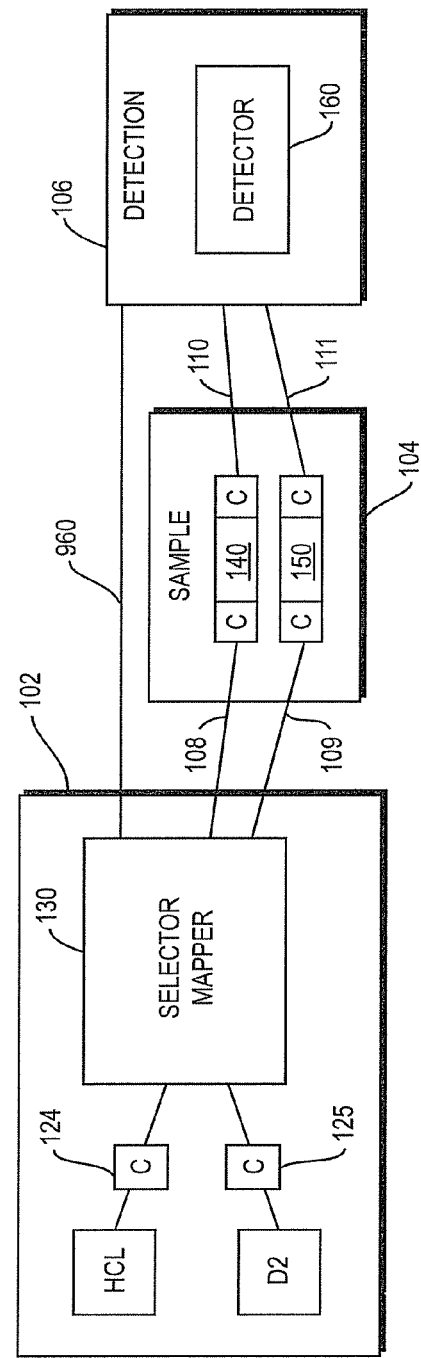
FIG. 7 is an alternative configuration of the system depicted in FIG. 1.

Alternatively, as depicted in FIG. 7, the system may be configured with a separately routed, dedicated reference fiber cable 960. The detector 160 thus operates with three sensing regions or three sensors (not shown). In this configuration, the system controller 184 controls the processor sub-system 194 to ensure that the signals from the selected atomizer are processed as measurement signals, the signals from the non-selected atomizer are not processed, and the signals from the dedicated reference path are processed as reference signals. The measurement path in this configuration is selectably interchangeable, to provide the system flexibility described above.

The systems described herein may be configured with more than two atomizers in selectable and interchangeable measurement and reference paths, with the user selecting one of the atomizers for sample measurement at a given time and either the user or the system controller assigning one of the non-selected atomizers to act as part of the reference path. The system controller instructs the processing sub-system 194 to process the signals associated with the selected processor as the measurement signals and, as appropriate, the signals associated with the non-selected assigned atomizer as the reference signals. In such a system, any or all of the non-selected atomizers may operate in stand-by mode and pass signals from the first to the second set of fiber optic cables, with only the signals from the non-selected atomizer that is assigned to the reference path being processed by the processing sub-system. As discussed, the reference path may instead be provided by a dedicated fiber optic cable. The multiple atomizer configuration of the system provides the same flexibility described above, since the measurement path and, as appropriate, the reference path, are selectable and interchangeable through the system.

The system may provide to a given atomizer different ratios or intensities of HCL and/or DU light when, for example, greater intensities of light may be required to perform an analysis. The selector/mapper may provide a mix of 60%/40% HCL/DU light, or other selected ratios such as 70%/30%, by appropriately mapping and bundling the light from the respective sources to the atomizers. The selector/mixer may similarly provide simultaneously to one of the atomizers various mixes of different wavelengths of light produced by two or more HCL's.

Alternatively, or in addition, a switching mechanism (not shown) may be employed to provide increased throughput to a given atomizer that utilizes only light from a single type of light source, such as an HCL, as opposed to light from both the HCL and a D2 lamp. When an atomizer that requires only the HCL light is selected, the switching mechanism mechanically connects a single light source to an additional fiber cable (not shown) that by-passes the selector/mapper and runs to the atomizer, such as the furnace 140. Otherwise, the switching mechanism provides light from both the HCL and the D2 lamp to the selector/mapper, which in-turn, provides mixed HCL and D2 light to both atomizers over the second set of fiber optic cables 108 and 109.

The foregoing description has been limited to a specific embodiment of this invention. It will be apparent, however, that variations and modifications may be made to the invention, such as the use of other light sources, for example, electrodeless discharge lamps, other types of atomizers, for example, cold vapor cells, in place of or in addition to the lamps and atomizers described above, the selector/mapper may map the light from particular light sources to sub-sets of the atomizers, light from multiple HCLs and/or EDLs may be mapped simultaneously to the atomizers through bundling of the associated optical fibers and a polychromatic detector may be used in place of the monochromatic detector, light from a single light source may be mapped to each atomizer, and so forth, with the attainment of some or all of its advantages. Therefore, it is the object of the appended claims to cover all such variations and modifications as come within the true spirit and scope of the invention.

What is claimed is:
1. A photonic measurement system including
one or more light sources;
at least two analysis chambers, wherein one or more of the analysis chambers contains a sample to be analyzed;
a first set of fiber optic cables that guide light produced by the one or more light sources to each of the analysis chambers;
a second set of fiber optic cables that guide light from the respective analysis chambers to a detector;
the detector configured to produce signals corresponding to intensities of light guided to the detector from respective cables of the second set of fiber optic cables;
a processing sub-system that processes signals provided by the detector; and
a system controller that controls the one or more light sources and the analysis chambers to operate a selected analysis chamber to perform a sample analysis and con- trols the processing sub-system to process the signals associated with the selected analysis chamber as measurement signals.

2. The photonic measurement system of claim 1 wherein the light sources are of first and second types, and
the first set of fiber optic cables includes a selector/mapper that bundles and maps optical fibers to guide light from each of the first and second types of light sources to respective analysis chambers.

3. The photonic measurement system of claim 2 wherein the processing sub-system processes signals associated with a non-selected analysis chamber as reference signals.

4. The photonic measurement system of claim 3 wherein the system is an atomic absorption spectrometer and the analysis chambers are a furnace atomizer and a flame atomizer.

5. The photonic measurement system of claim 4 wherein the first and second light sources are hollow cathode lamps and Deuterium lamps.

6. The photonic measurement system of claim 4 wherein the first and second light sources are electrodeless discharge lamps and Deuterium lamps.

7. The photonic measurement system of claim 4 further including a switching mechanism that provides light from the first source type to a first selected analysis chamber and light from both first and second source types to a different selected analysis chamber.

8. The photonic measurement system of claim 2 further including
a third fiber optic cable that provides light from the first and second types of light sources to the detector; and
the processing sub-system processes signals associated with the third fiber optic cable as reference signals.

9. The photonic measurement system of claim 1 further including
a first plurality of couplers to couple light to and from the fiber optic cables in the first set, and
a second plurality of couplers to couple light to the fiber optic cables in the second set.

10. The photonic measurement system of claim 9 wherein the first and second couplers are off-axis ellipsoid mirrors.

11. The photonic measurement system of claim 9 further including
multiple light sources of the first type that produce light in respective wavelengths, and
means for positioning the corresponding coupler relative to a given one of the light sources of the first type to couple light of a selected wavelength to the first set of fiber optic cables.

12. The photonic measurement system of claim 9 further including
multiple light sources of the first type that produce light in respective wavelengths for absorption, and
means for positioning the light sources with respect to the corresponding coupler to couple light from a selected light source of the first type to the first set of fiber optic cables.

13. The photonic measurement system of claim 9 further including
multiple light sources of the first type that produce light in respective wavelengths for absorption, and
multiple couplers that couple light from the respective multiple light sources to the first set of fiber optic cables.

14. The photonic measurement system of claim 1 wherein the system is an atomic absorption spectrometer and all of the analysis chambers are furnaces.

15. The photonic measurement system of claim 1 wherein the system performs one of inductively coupled plasma optical emission spectroscopy, optical detection in liquid chromatography, UltraViolet/visible spectroscopy and UltraViolet/visible near infrared spectroscopy.

16. The photonic measurement system of claim 1 wherein one or both of the first and second sets of fiber optic cables consist of non-solarizing UV grade optical fibers.

17. A method of operating an atomic absorption spectrometer comprising
selecting an atomizer from at least two atomizers that are configured within respective guided light paths from light sources to a detector; and
operating a processing sub-system that is configured to receive signals from the detector to process signals associated with the selected atomizer as measurement signals.

18. The method of claim 17 further including operating the processing sub-system to process signals associated with a given non-selected atomizer as reference signals.

19. The method of claim 18 further including
making a new atomizer selection; and
operating the processing sub-system to processing signals associated with the newly selected atomizer as measurement signals and signals associated with a given non-selected atomizer as reference signals.

20. A photonic measurement system including
a source module including one or more light sources;
a sample module including at least two analysis chambers, wherein one or more of the analysis chambers contains a sample to be analyzed;
a detection module including a detector that produces signals associated with each of the analysis chambers;
a first set of fiber optic cables that guide light from the one or more light sources to each of the analysis chambers;
a second set of fiber optic cables that guide light from each of the analysis chambers to the detector;
a processing sub-system that processes the signals produced by the detector; and
a system controller that controls the one or more light sources and the analysis chambers to operate a selected analysis chamber to perform a sample analysis and controls the processing sub-system to process the signals associated with the selected analysis chamber as measurement signals.

21. The photonic measurement system of claim 20 wherein the light sources are different types of light sources, and
the first set of fiber optical cables includes optical fibers that guide light from each of the different types of light sources and a mapper/selector that bundles and maps the optical fibers to guide light from each of the two types of light sources to each of the analysis chambers.

22. The photonic measurement system of claim 21 wherein the system controller further operates the detection module to process as reference signals the signals associated with a given analysis chamber that is not selected.

23. The photonic measurement system of claim 22 wherein the system is an atomic absorption spectrometer and the analysis chambers are a furnace atomizer and a flame atomizer.

24. The photonic measurement system of claim 23 wherein one or both of the first and second sets of fiber optic cables consist of non-solarizing UV grade optical fibers.

25. An atomic absorption spectrometer including
one or more light sources, wherein the light sources are of first and second types;

at least two analysis chambers, wherein at least one of the analysis chambers is a furnace atomizer and at least one of the analysis chambers is a flame atomizer;

a first set of fiber optic cables that guide light produced by the one or more light sources to each of the analysis chambers, wherein the first set of optic cables includes a selector/mapper that maps optical fibers to guide light from each of the first and second types of light sources to respective analysis chambers;

a second set of fiber optic cables that guide light from the respective analysis chambers to a detector;

the detector configured to produce signals corresponding to intensities of light guided to the detector from respective cables of the second set of fiber optic cables;

a processing sub-system that processes signals provided by the detector, wherein the signals associated with a non-selected analysis chamber are processed as reference signals; and a system controller that controls the one or more light sources and the analysis chambers to operate a selected analysis chamber to perform a sample analysis and controls the processing sub-system to process the signals associated with the selected analysis chamber as measurement signals.

26. An atomic absorption spectrometer including one or more light sources;

at least two analysis chambers, wherein all of the analysis chambers are furnaces;

a first set of fiber optic cables that guide light produced by the one or more light sources to each of the analysis chambers;

a second set of fiber optic cables that guide light from the respective analysis chambers to a detector;

the detector configured to produce signals corresponding to intensities of light guided to the detector from respective cables of the second set of fiber optic cables;

a processing sub-system that processes signals provided by the detector; and a system controller that controls the one or more light sources and the analysis chambers to operate a selected analysis chamber to perform a sample analysis and controls the processing sub-system to process the signals associated with the selected analysis chamber as measurement signals.

\* \* \* \* \*

UNITED STATES PATENT AND TRADEMARK OFFICE
CERTIFICATE OF CORRECTION

PATENT NO. : 8,541,741 B2  
APPLICATION NO. : 12/949383  
DATED : September 24, 2013  
INVENTOR(S) : Juan C. Ivaldi et al.

Page 1 of 1

It is certified that error appears in the above-identified patent and that said Letters Patent is hereby corrected as shown below:

In the Specification

In col. 1, line 52 should read:  
of the precisely aligned configuration of ~~minors~~ mirrors and beam In col. 1, line 54 should read:  
further plurality of ~~minors~~ mirrors that tightly couple the light to the In col. 4, line 41 should read:  
~~minor~~ mirror. In the example, the ~~minor~~ mirror reflects the light with a 90°

In col. 4, line 60 should read:  
~~minor~~ mirror may be used instead of an elliptical mirror.

In col. 4, line 64 should read:  
point of the ~~minor~~ mirror is within the entrance 352 of the core, Signed and Sealed this  
Third Day of December, 2013

Margaret A. Focarino  
*Commissioner for Patents of the United States Patent and Trademark Office*